(12) United States Patent
Jiang et al.

(10) Patent No.: US 7,795,455 B2
(45) Date of Patent: Sep. 14, 2010

(54) CRYSTALLINE DULOXETINE HYDROCHLORIDE

(75) Inventors: Wei Ping Jiang, Chongqing (CN); Chun Rong Jia, Chongqing (CN)

(73) Assignees: Chongqing Shenghuaxi Pharmaceuticals Co. Ltd., Chongqing (CN); Arrow International Limited, Valetta (MT)

( * ) Notice: Subject to any disclaimer, the term of this patent is extended or adjusted under 35 U.S.C. 154(b) by 628 days.

(21) Appl. No.: 11/821,460

(22) Filed: Jun. 22, 2007

(65) Prior Publication Data

US 2008/0021091 A1   Jan. 24, 2008

(30) Foreign Application Priority Data

Jun. 23, 2006  (GB)  ................. 0612509.0
Jan. 16, 2007  (GB)  ................. 0700830.3

(51) Int. Cl.
 *C07D 333/36*  (2006.01)
(52) U.S. Cl. ....................................... 549/68
(58) Field of Classification Search ............ 549/68
 See application file for complete search history.

(56) References Cited

U.S. PATENT DOCUMENTS

| | | | |
|---|---|---|---|
| 4,956,388 A | 9/1990 | Robertson et al. | |
| 5,023,269 A | 6/1991 | Robertson et al. | |
| 5,491,243 A | 2/1996 | Berglund | |
| 2005/0197503 A1 | 9/2005 | Schiffers et al. | |

FOREIGN PATENT DOCUMENTS

| | | |
|---|---|---|
| EP | 0 650 965 A1 | 5/1995 |
| EP | 1 820 800 A1 | 8/2007 |
| GB | 0612509.0 | 10/2006 |
| GB | 0700830.3 | 5/2007 |
| WO | WO 2005/019199 A1 | 3/2005 |
| WO | WO 2005/108386 A1 | 11/2005 |
| WO | WO 2006/027798 A2 | 3/2006 |
| WO | WO 2006/045255 A1 | 5/2006 |
| WO | WO 2006/055964 A2 | 5/2006 |
| WO | WO 2006/058121 A1 | 6/2006 |
| WO | WO 2006/071868 A2 | 7/2006 |
| WO | WO 2006/081515 A2 | 8/2006 |
| WO | WO 2006/099468 A2 | 9/2006 |
| WO | PCT/GB2007/002324 | 6/2007 |
| WO | WO 2007/077580 A2 | 7/2007 |
| WO | PCT/GB2007/002324 | 10/2007 |

OTHER PUBLICATIONS

Wheeler, W. et al., Journal of Labelled Compounds and Radiopharmaceuticals, vol. 36, No. 3, pp. 213-223 (1995), John Wiley & Sons, Ltd.

Synthon BV, "Duloxetine hydrochloride polymorphs," 498011, Research Disclosure, Oct. 2005, pp. 1129-1131.

*Primary Examiner*—Taofiq A Solola
(74) *Attorney, Agent, or Firm*—Sunstein Kann Murphy & Timbers LLP

(57) ABSTRACT

Crystalline duloxetine hydrochloride, compositions containing the same and methods for the production thereof.

57 Claims, 3 Drawing Sheets

CRYSTALLINE DULOXETINE HYDROCHLORIDE

CROSS-REFERENCE TO RELATED APPLICATIONS

This application claims priority from Great Britain application serial number GB0612509.0 filed 23 Jun. 2006, and Great Britain application serial number GB0700830.3 filed 16 Jan. 2007.

FIELD OF THE INVENTION

The present invention relates to crystalline duloxetine hydrochloride, to compositions containing the same and to methods for the formation thereof.

BACKGROUND OF THE INVENTION

Duloxetine hydrochloride is a potent dual reuptake inhibitor of serotonin and norepinephrine possessing comparable affinities in binding to serotonin and norepinephrine transport sites. Duloxetine hydrochloride has, therefore, been implicated in the treatment of various diseases related to these effects. For example, duloxetine hydrochloride is the active ingredient of the antidepressant drug Cymbalta®. It is also used to target pain related to diabetic neuropathy and stress urinary incontinence.

Preparation of duloxetine hydrochloride has been disclosed elsewhere, for example in U.S. Pat. No. 5,023,269. Crystalline forms of the free base of duloxetine and their preparation have been reported in WO 2005/108386. The amorphous form of duloxetine hydrochloride salt together with its preparation has been reported in WO 2005/019199.

There is no generally applicable method for preparing a crystalline form of an amorphous drug. For example, it is impossible to know without experimentation whether any crystalline form of a given compound exists. Even once it has been found that a drug can be crystallised, extensive experimentation is usually required before a repeatable and quantifiable process is identified from which the crystalline form can be isolated. In this respect, several independently variable conditions, such as the nature of solvent, concentration of solvent and temperature, must be correctly identified in order to elucidate a suitable process. Indeed, to date, there have been no reports describing isolation or production of crystalline duloxetine hydrochloride.

It is, therefore, an object of the present invention to provide crystalline forms of duloxetine hydrochloride together with methods for the production thereof.

SUMMARY OF THE INVENTION

According to a first aspect of the present invention, there is provided crystalline duloxetine hydrochloride.

According to another aspect of the present invention, there is provided crystalline duloxetine hydrochloride which exhibits an X-ray diffraction pattern comprising peaks expressed in degrees two-theta at approximately 18.0±0.2, 18.77±0.2, 20.78±0.2 and 27.86±0.2. The degree of error is preferably ±0.1.

According to a further aspect of the present invention, there is provided crystalline duloxetine hydrochloride which exhibits an X-ray diffraction pattern comprising peaks expressed in degrees two-theta at approximately 9.52±0.2, 13.82±0.2, 17.98±0.2, 18.77±0.2, 20.78±0.2, 23.24±0.2, 24.41±0.2, 26.35±0.2 and 27.86±0.2. The degree of error is preferably ±0.1.

There is also provided by the present invention, crystalline duloxetine hydrochloride which exhibits an X-ray diffraction pattern substantially the same as shown in FIG. 2.

Further provided is crystalline duloxetine hydrochloride which exhibits a solid $C^{13}$ Nuclear Magnetic Resonance (NMR) spectrum comprising chemical shifts expressed in parts per million at approximately 126.2, 120.9, 105.1, 75.9 and 33.9. Where appropriate the tolerance in these and other NMR values is up to ±1.

Additionally provided is crystalline duloxetine hydrochloride which exhibits a solid $C^{13}$ NMR spectrum comprising chemical shifts expressed in parts per million at approximately 151.3, 146.4, 135.0, 126.2, 120.9, 105.1, 75.9, 49.2, 38.2 and 33.9.

In another embodiment, there is provided crystalline duloxetine hydrochloride which exhibits a solid $C^{13}$ NMR spectrum substantially the same as shown in FIG. 1.

Preferably, the crystalline duloxetine hydrochloride has a purity of at least 95%, more preferably at least 98%.

According to a further aspect of the present invention, there is provided a method for the preparation of crystalline duloxetine hydrochloride, the method comprising:

(a) dissolving duloxetine in a first organic solvent to form a first solution;
(b) adding the first solution to a second organic solvent solution comprising HCl to form a second solution;
(c) allowing duloxetine hydrochloride to crystallize out from the solution; and
(d) collecting the crystallized duloxetine hydrochloride.

The first method may also comprise the following additional steps prior to step (c):

(b1) removing the solvents to form a residue; and
(b2) dissolving the residue in a third organic solvent to form a third solution;

Preferably, the third organic solvent is a $C_1$ to $C_6$ ester, more preferably ethyl acetate.

Preferably, the residue is dissolved in the third organic solvent in a ratio of about 20 ml third organic solvent for about every 3 g of duloxetine used in step (a).

Preferably, the first organic solvent is a heterocyclic organic compound or a $C_1$ to $C_6$ nitrile compound, more preferably, tetrahydrofuran or acetonitrile.

In preferred embodiments, the second organic solvent is an alcohol, more preferably a straight or branched $C_1$ to $C_6$ alcohol, further preferably ethanol.

Preferably, the duloxetine is dissolved in the first organic solvent in a ratio of about 20 ml first organic solvent for about every 3 g of duloxetine.

In preferred aspects, the second organic solvent comprises about 20% HCl.

It is also preferred that the first solution is added to the second organic solvent at around 0° C. The first solution is preferably added to the second organic solvent with stirring.

Preferably, the solvents are removed under reduced pressure.

In order to maximize crystallization, the duloxetine hydrochloride may be allowed to crystallize out from the solution during a period of cooling at around 0° C. to around 10° C. Preferably, the duloxetine hydrochloride is allowed to crystallize out from the solution during a period of about 10 hours.

Preferably, the crystallized duloxetine hydrochloride is collected by filtration. The collected crystallized duloxetine hydrochloride is preferably washed and then dried.

In preferred embodiments, the collected crystallized duloxetine hydrochloride is washed with a $C_1$ to $C_6$ ester or a $C_1$ to $C_6$ nitrile compound, more preferably ethyl acetate or acetonitrile.

Preferably, the method comprises the following additional steps for the preparation of duloxetine for use in step (a):
(i) placing duloxetine oxalate into a solution of a fourth organic solvent and water;
(ii) adding aqueous ammonia solution for dissolving the duloxetine oxalate;
(iii) isolating a separated organic layer;
(iv) washing the organic layer with saturated brine;
(v) drying the organic layer; and
(vi) removing the solvents from the organic layer.

Preferably, the fourth organic solvent is a $C_1$ to $C_6$ ester, more preferably ethyl acetate.

The duloxetine oxalate is preferably placed into a solution of the fourth organic solvent and water at a ratio of about 300 ml fourth organic solvent and water solution for about every 39 g of duloxetine oxalate.

Preferably, the solution of a fourth organic solvent and water contains about 1 ml fourth organic solvent for about every 1 ml water.

The aqueous ammonia is preferably added under stirring.

Preferably, an aqueous layer is isolated and then washed with the fourth organic solvent.

Preferably, the organic layer is dried with anhydrous sodium sulphate.

According to another aspect of the present invention there is provided a method for the preparation of crystalline duloxetine hydrochloride, the method comprising:
(a) placing duloxetine oxalate into a solution of organic solvent and water;
(b) adding aqueous ammonia solution for dissolving the duloxetine oxalate;
(c) isolating a separated organic layer;
(d) washing the organic layer with saturated brine;
(e) drying the organic layer;
(f) decolorizing the organic layer with a decolorizing agent;
(g) removing the decolorizing agent to form an organic solution;
(h) introducing gaseous hydrochloride into the organic solution; and
(i) collecting crystalline duloxetine hydrochloride from the organic solution.

Preferably, the organic solvent is a $C_1$ to $C_6$ ester, more preferably ethyl acetate.

In preferred embodiments, the duloxetine oxalate is placed into the solution of the organic solvent and water at a ratio of about 1 part organic solvent and water solution for about every 1 part duloxetine oxalate.

The solution of organic solvent and water preferably contains about 1 ml organic solvent for about every 1 ml water.

Preferably, the aqueous ammonia solution is added under stirring.

Preferably, the collected crystalline duloxetine hydrochloride is washed with an organic solvent.

In preferred aspects, the collected crystalline duloxetine hydrochloride is dried. Further preferably, the collected crystalline duloxetine hydrochloride is dried under vacuum.

Preferably, the gaseous hydrochloride is introduced under agitation. In preferred methods, gaseous hydrochloride is introduced until the solution reaches a pH of around 2 to 4.

According to another aspect of the present invention there is provided a method for the preparation of crystalline duloxetine hydrochloride, the method comprising:
(a) providing a solution of duloxetine free base in an organic solvent;
(b) mixing the organic solution with aqueous ammonium chloride solution; and
(c) acidifying the solution to a pH of 1 to 4 with hydrochloric acid.

Preferably, the method comprises:
(a) providing a solution of duloxetine free base in an organic solvent;
(b) mixing the organic solution with aqueous ammonium chloride solution;
(c) acidifying the solution to a pH of 1 to 4 with hydrochloric acid; and
(d) collecting crystalline duloxetine hydrochloride from the organic solution.

More preferably, the method comprises:
(a) providing a solution of duloxetine free base in an organic solvent;
(b) mixing the organic solution with aqueous ammonium chloride solution;
(c) acidifying the solution to a pH of 1 to 4 with hydrochloric acid;
(d) isolating a separated organic layer; and
(e) collecting crystalline duloxetine hydrochloride from the organic solution.

Yet more preferably, the method comprises:
(a) providing a solution of duloxetine free base in an organic solvent;
(b) mixing the organic solution with aqueous ammonium chloride solution;
(c) acidifying the solution to a pH of 1 to 4 with hydrochloric acid;
(d) isolating a separated organic layer;
(e) drying the organic layer;
(f) decolorizing the organic layer with a decolorizing agent;
(g) removing the organic solvent to form a residue;
(h) dissolving the residue in an organic solvent; and
(i) collecting crystalline duloxetine hydrochloride from the organic solution.

Yet more preferably, the method comprises:
(a) adding duloxetine oxalate to a mixture of organic solvent and water;
(b) adding aqueous ammonia solution for dissolving the duloxetine oxalate;
(c) isolating a separated organic layer;
(d) saturating the aqueous layer with sodium chloride;
(e) extracting the aqueous layer with an organic solvent;
(f) combining the organic layers;
(g) washing the organic solution with saturated brine;
(h) mixing the organic solution with aqueous ammonium chloride solution;
(i) acidifying the solution to a pH of 1 to 4 with hydrochloric acid;
(j) isolating a separated organic layer;
(k) drying the organic layer;
(l) decolorizing the organic layer with a decolorizing agent;
(m) removing the decolorizing agent to form an organic solution;
(n) removing the organic solvent to form a residue;
(o) dissolving the residue in an organic solvent; and
(p) collecting crystalline duloxetine hydrochloride from the organic solution.

Preferably, the duloxetine free base is provided in an organic solvent selected from ethyl acetate, methyl acetate, dichloromethane, THF, methanol, ethanol, isopropanol, acetonitrile, hexane, heptane, chloroform, acetone, diethyl ether, diisopropyl ether and toluene and mixtures thereof.

More preferably, the organic solvent comprises ethyl acetate.

Yet more preferably, the organic solvent comprises a mixture of ethyl acetate and dichloromethane.

Most preferably, the organic solvent comprises 5:2 (w/w) ethyl acetate:dicholoromethane.

Preferably, the ammonium chloride solution is saturated.

Preferably, the hydrochloric acid is dilute, e.g. 0.1M, 1M or 2M HCl.

Preferably, the solution is acidified to pH 2 to 4.

Most preferably, the solution is acidified to about pH 2.

Preferably, the drying agent is anhydrous sodium sulphate.

Preferably, the decolorising agent is active charcoal.

Preferably, the residue is formed by removing the organic solvent by distillation under reduced pressure.

Preferably, the duloxetine hydrochloride residue is dissolved and the crystalline duloxetine hydrochloride isolated from an organic solvent selected from ethyl acetate, methyl acetate, dichloromethane, THF, methanol, ethanol, isopropanol, acetonitrile, hexane, heptane, chloroform, acetone, diethyl ether, diisopropyl ether and toluene and mixtures thereof.

Most preferably, the organic solvent comprises ethyl acetate.

Preferably, the crystallized duloxetine hydrochloride is collected by filtration. The collected crystallized duloxetine hydrochloride is preferably washed and then dried.

Accordingly, another preferred embodiment of the invention comprises:
(a) adding duloxetine oxalate to a mixture of ethyl acetate, dichloromethane and water;
(b) adding aqueous ammonia solution for dissolving the duloxetine oxalate;
(c) isolating a separated organic layer;
(d) saturating the aqueous layer with sodium chloride;
(e) extracting the aqueous layer with dichloromethane;
(f) combining the organic layers;
(g) washing the organic solution with saturated brine;
(h) mixing the organic solution with saturated aqueous ammonium chloride solution;
(i) acidifying the solution to pH 2 with dilute hydrochloric acid;
(j) isolating a separated organic layer;
(k) drying the organic layer with anhydrous sodium sulphate;
(l) decolorizing the organic layer with active charcoal;
(m) removing the charcoal from the organic solution;
(n) removing the organic solvent by distillation under reduced pressure to form a residue;
(o) dissolving the residue in ethyl acetate; and
(p) collecting crystalline duloxetine hydrochloride from the organic solution.

According to a further aspect of the present invention, there is provided crystalline duloxetine hydrochloride prepared by any of the methods above. Preferably, the crystalline duloxetine hydrochloride has a purity of at least 95%, more preferably at least 98%.

Accordingly, the present invention describes a novel crystalline form of duloxetine hydrochloride and a process to prepare it.

It is anticipated that the crystalline form of duloxetine hydrochloride disclosed herein will be useful in the treatment of a variety of diseases which are prevented, ameliorated or eliminated by the administration of a serotonin and/or norepinephrine reuptake inhibitor. Examples of such diseases include depression, pain related to diabetic neuropathy and stress urinary incontinence, obesity, alcoholism, loss of memory, anxiety and smoking.

According to another aspect of the present invention, there is therefore provided a pharmaceutical composition comprising crystalline duloxetine hydrochloride as described herein.

According to a further aspect, there is provided a composition for treating a disease which is prevented, ameliorated or eliminated by the administration of a serotonin and/or norepinephrine reuptake inhibitor, the composition comprising crystalline duloxetine hydrochloride as described herein.

Preferably, the disease is selected from depression, pain related to diabetic neuropathy and stress urinary incontinence, obesity, alcoholism, loss of memory, anxiety and smoking.

There is also provided a method of treating a disease which is prevented, ameliorated or eliminated by the administration of a serotonin and/or norepinephrine reuptake inhibitor, the method comprising administering to a patient a therapeutically effective amount of crystalline duloxetine hydrochloride as described herein, or of the pharmaceutical composition as described herein.

Preferably, the disease is selected from depression, pain related to diabetic neuropathy and stress urinary incontinence, obesity, alcoholism, loss of memory, anxiety and smoking.

By a therapeutically effective amount, it is meant an amount which is capable of preventing, ameliorating or eliminating the diseases mentioned herein.

The crystalline duloxetine hydrochloride can be mixed with a carrier, diluent or excipient therefore, all of which are well known in the art. For example, suitable carriers may include pills, powders, lozenges, sachets, cachets, elixirs, suspensions, emulsions, solutions, syrups, aerosols, ointments, soft and hard gelatine capsules, suppositories, sterile injectable solutions and sterile packaged powders.

There are many advantages to providing a crystalline form of duloxetine hydrochloride compared to an amorphous form. A crystalline form of the drug can be easily purified by crystallisation and recrystallisation. Compared to other methods of purification, it is also cheaper and more convenient to perform crystallisation on a large scale. Furthermore, a crystalline form may be more stable than an amorphous form.

BRIEF DESCRIPTION OF THE DRAWINGS

An example of the present invention will now be described in detail with reference the accompanying figures.

DETAILED DESCRIPTION OF THE INVENTION

Figure 1:
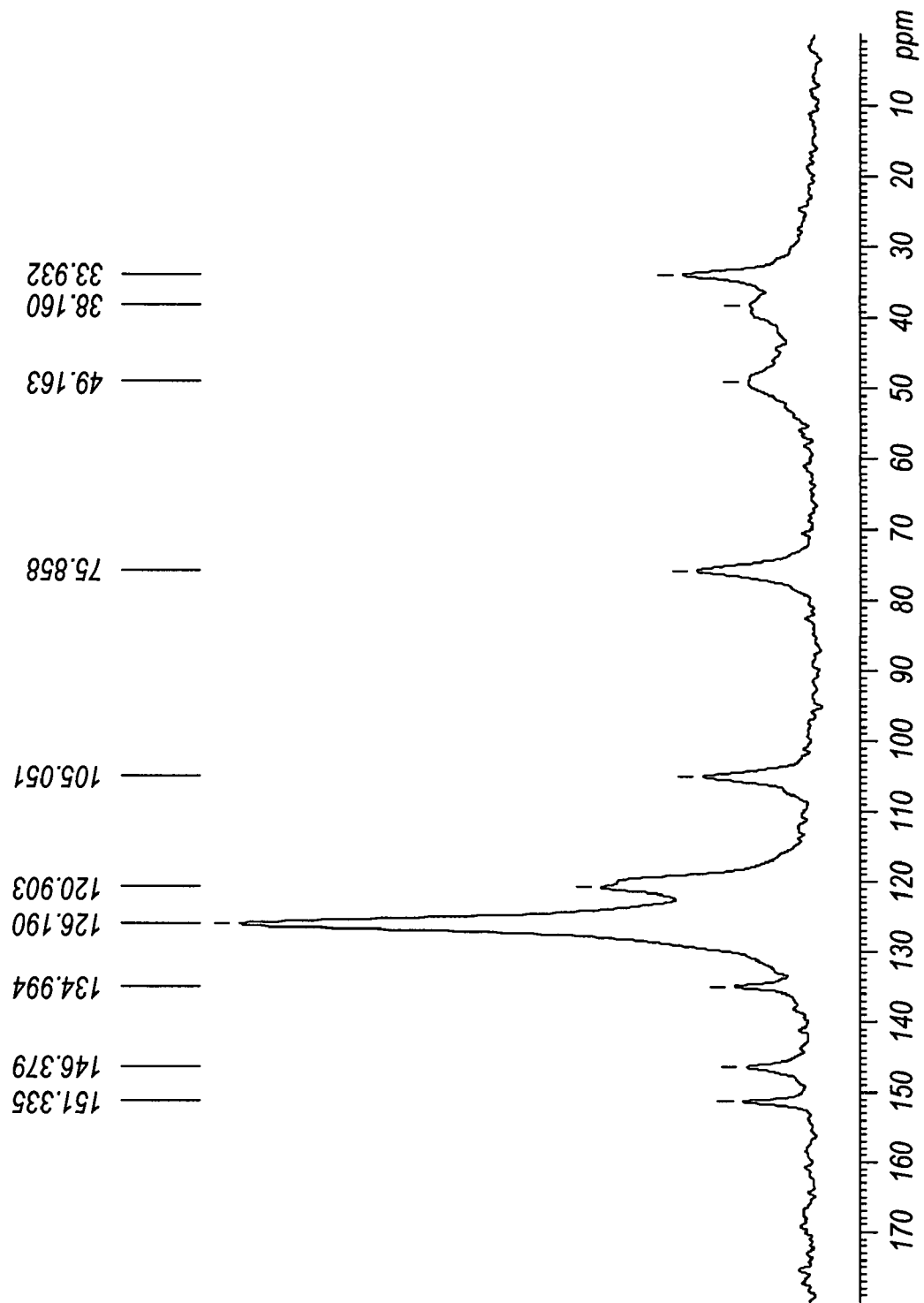
FIG. 1 shows the solid $C^{13}$ NMR spectrum for the crystalline form of the present invention.
Figure 2:
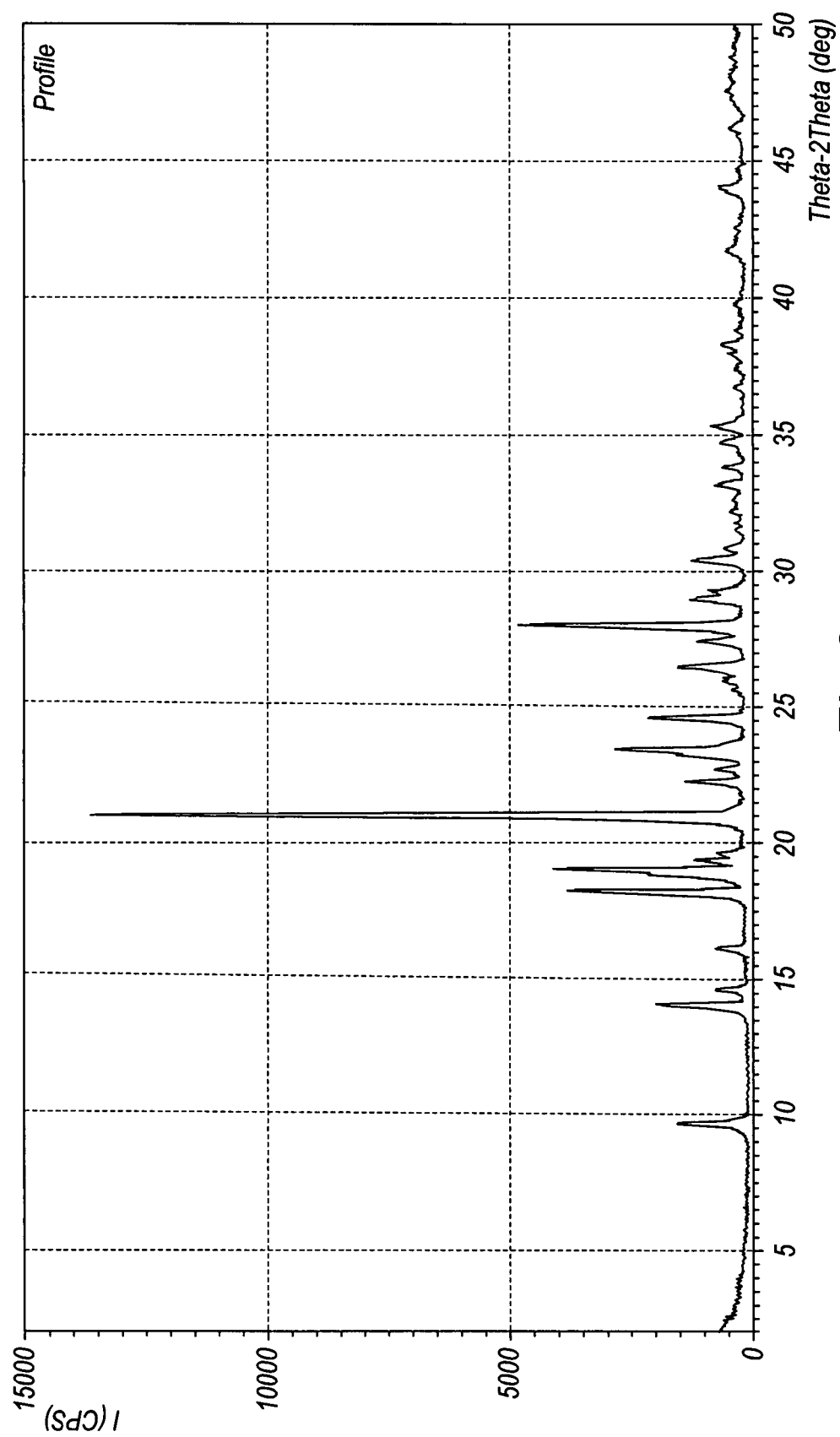
FIG. 2 shows the X-ray powder diffraction (XRD) spectrum for the crystalline form of the present invention.
Figure 3:
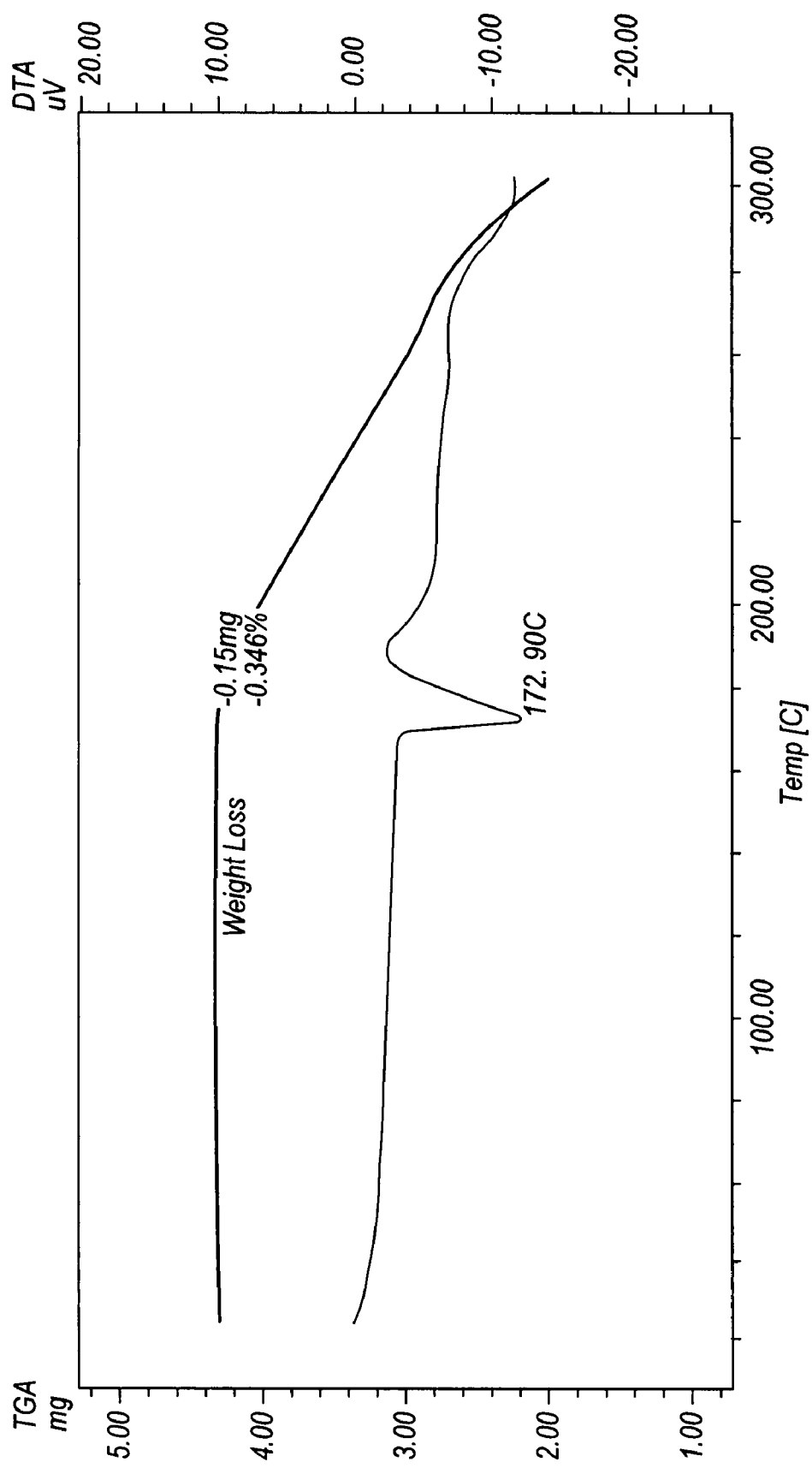
FIG. 3 shows Thermogravimetric (TGA) and Differential Thermal Analysis (DTA) thermograms for the crystalline form of the present invention.

Duloxetine oxalate salt was initially prepared following the procedure given in EP273658 (corresponding to U.S. Pat. Nos. 5,023,269 and 4,956,388, each hereby incorporated by reference). Duloxetine was then freed from the oxalic acid and converted directly to its hydrochloride salt by the introduction of hydrochloride in organic solvent.

The isolated crystalline duloxetine hydrochloride was fully characterized by Differential Scanning Calorimetry (DSC), solid carbon-13 NMR and X-ray powder diffraction.

Crystallization

Example 1

Duloxetine oxalate (40 kg), water (20 kg) and ethyl acetate (20 kg) were added sequentially into a reactor. Concentrated ammonia solution was then added slowly to the agitated mixture until all solid was dissolved. Agitation of the mixture was stopped and the mixture allowed to settle to form two layers. The separated aqueous layer was washed with ethyl acetate (5 kg×2). The combined organic solution was washed twice with saturated brine and then dried with anhydrous sodium sulphate. After removing the drying sodium sulphate, the filtrate solution was decolorized by adding activate charcoal (100 g) and stirring at room temperature for 30 minutes. The charcoal was removed by filtration. The resultant clear ethyl acetate solution was introduced with gaseous hydrochloride under agitation until it became acidic (pH was 2-4). A white crystalline solid came out slowly from the acidic solution. More solid came out by stirring for an extra half an hour. The white solid was collected by filtration and washed with more ethyl acetate, then dried under vacuum at 40-50° C. for 8 hours (2.4 kg dried crystalline solid, 70% yield, assay more than 99%). The crystalline form, designated as Form I, was thus obtained.

Example 2

Free Duloxetine Preparation:

Duloxetine oxalate (38.7 g) was placed into 300 ml of an ethyl acetate/water (1:1) mixture. Aqueous ammonium solution was added to dissolve the solid completely under stirring. The separated aqueous layer was washed with ethyl acetate twice. The combined organic solution was then washed with saturated brine, and dried with anhydrous sodium sulphate. The free duloxetine (26 g) was obtained as an oil by removing the solvents from the filtrate solution.

Crystallization of Duloxetine Hydrochloride:

The free duloxetine oil (3 g) was dissolved in THF (20 ml). The resulting solution was then added to an ethanol solution containing 20% HCl with stirring at 0° C. The solvents were removed under reduced pressure after addition. The residue was dissolved with ethyl acetate (20 ml) and cooled at 0-10° C. for 10 hours. The crystalline duloxetine hydrochloride salt was then collected by filtration, washed with ethyl acetate and dried (2 g, 60% yield, m.p. 156-160° C.). The assay of the material was 99.2% by HPLC, and its optical purity was 99.5% (chiral column HPLC). The DTA result shown m.p. was 172.9° C. The crystalline form, designated as Form I, was thus obtained.

Example 3

Free Duloxetine Preparation:

Duloxetine oxalate (38.7 g) was placed into 300 ml of an ethyl acetate/water (1:1) mixture. Aqueous ammonium solution was added to dissolve the solid completely under stirring. The separated aqueous layer was washed with ethyl acetate twice. The combined organic solution was then washed with saturated brine, and dried with anhydrous sodium sulphate. The free duloxetine (26 g) was obtained as an oil by removing the solvents from the filtrate solution.

Crystallization of Duloxetine Hydrochloride:

The free oily duloxetine (3 g) was dissolved in acetonitrile (20 ml), then an ethanol solution (2 ml) containing 20% HCl was added to the solution under stirring at 0° C. The product crystallized out after the solution was kept cooling at 0-10° C. for 10 hours. The crystalline salt was collected by filtration, washed with more acetonitrile and dried (2 g, 60% yield, m.p. 146-153° C.). Its purity was determined to be 96.5%, and its optical purity was 99.9% (chiral column HPLC). The DTA result shown m.p. was 167.7° C. The crystalline form, designated as Form I, was thus obtained.

Example 4

Duloxetine oxalate (4.0 kg), water (20 kg), ethyl acetate (20 kg) and dichloromethane (4 kg) were added sequentially into a reactor. Concentrated ammonia solution was then added slowly to the agitated mixture until all of the solid had dissolved. Agitation of the mixture was stopped and the mixture allowed to settle to form two layers. The separated aqueous layer was saturated by addition of sodium chloride then washed with dichloromethane (2 kg×2). The combined organic solutions were washed twice with saturated brine then introduced with saturated ammonium chloride solution (20 kg) under agitation at room temperature (about 25 to 30° C.) and was made acidic (pH=2) by adding dilute hydrochloric acid solution. The mixture was stirred for a further 2 hours and the organic layer was then separated. Sodium sulphate (anhydrous) was added to the organic layer and then filtered off. The filtrate was decolorized by adding active charcoal (100 g), stirring at room temperature for 30 minutes and then removing the charcoal by filtration. The solvent of the filtrate was removed by distillation under reduced pressure and the residue was dissolved in ethyl acetate (20 kg). The product crystallised out of solution as a white solid and the mixture was stirred for 30 minutes to complete the process. The solid was collected by filtration, washed with ethyl acetate and dried under vacuum at 40 to 50° C. for 8 hours to give 2.7 kg of crystalline product. Yield>70%, assay>99%, enantiomeric excess>99% by HPLC, melting point 158 to 160° C.

TABLE 1

The XRD spectrum for the crystalline form obtained according to the examples above.

| 2theta (degree) | I/I$_0$ | d (A) |
| --- | --- | --- |
| 9.523 | 8 | 9.279 |
| 13.818 | 10 | 6.403 |
| 17.978 | 19 | 4.930 |
| 18.773 | 21 | 4.722 |
| 20.782 | 100 | 4.270 |
| 23.239 | 15 | 3.824 |
| 24.413 | 10 | 3.643 |
| 26.346 | 8 | 3.380 |
| 27.859 | 34 | 3.199 |

TABLE 2

TGA/DTA parameters

| | |
| --- | --- |
| Detector | DTG-60H |
| Sample Weight | 4.330 mg |
| Temperature Rate | 10° C. |
| Hold Temperature | 300° C. |
| Hold Time | 0 min |

The invention claimed is:

1. A method for the preparation of crystalline duloxetine hydrochloride, the method comprising:

(a) dissolving duloxetine in a first organic solvent to form a first solution;

(b) adding the first solution to a second organic solvent comprising HCl to form a second solution;
(c) allowing duloxetine hydrochloride to crystallize out from the second solution; and
(d) collecting the crystallized duloxetine hydrochloride;
wherein the first organic solvent is a heterocyclic organic compound, a $C_1$ to $C_6$ nitrile compound, or a combination of a heterocyclic organic compound and a $C_1$ to $C_6$ nitrile compound.

2. The method of claim 1, wherein the first organic solvent is tetrahydrofuran or acetonitrile.

3. The method of claim 1, further comprising, prior to step (c):
(b1) removing the first and second organic solvents to form a residue; and
(b2) dissolving the residue in a third organic solvent to form a third solution.

4. The method of claim 3, wherein the third organic solvent is a $C_1$ to $C_6$ ester.

5. The method of claim 4, wherein the third organic solvent is ethyl acetate.

6. The method of claim 3, wherein the residue is dissolved in the third organic solvent in a ratio of about 20 ml third organic solvent for about every 3 g of duloxetine used in step (a).

7. The method of claim 1, wherein the second organic solvent is an alcohol.

8. The method of claim 7, wherein the second organic solvent is ethanol.

9. The method of claim 1, wherein the duloxetine is dissolved in the first organic solvent in a ratio of about 20 ml first organic solvent for about every 3 g of duloxetine.

10. The method of claim 1, wherein the second organic solvent comprises about 20% HCl.

11. The method of claim 1, wherein the first solution is added to the second organic solvent at around 0° C.

12. The method of claim 1, wherein the first solution is added to the second organic solvent with stirring.

13. The method of claim 1, wherein the solvents are removed under reduced pressure.

14. The method of claim 1, wherein duloxetine hydrochloride is allowed to crystallize out from the second solution during a period of cooling at about 0° C. to about 10° C.

15. The method of claim 1, wherein duloxetine hydrochloride is allowed to crystallize out from the second solution during a period of about 10 hours.

16. The method of claim 1, wherein the crystallized duloxetine hydrochloride is collected by filtration.

17. The method of claim 1, wherein the collected crystallized duloxetine hydrochloride is washed and then dried.

18. The method of claim 17, wherein the collected crystallized duloxetine hydrochloride is washed with a $C_1$ to $C_6$ ester or a $C_1$ to $C_6$ nitrile compound.

19. The method of claim 18, wherein the collected crystallized duloxetine hydrochloride is washed with ethyl acetate or acetonitrile.

20. The method of claim 1, further comprising, prior to step (a):
(i) placing duloxetine oxalate into a solution of a fourth organic solvent and water;
(ii) adding aqueous ammonia solution for dissolving the duloxetine oxalate;
(iii) isolating a separated organic layer;
(iv) washing the organic layer with saturated brine;
(v) drying the organic layer; and
(vi) removing the fourth solvent from the organic layer.

21. The method of claim 20, wherein the fourth organic solvent is a $C_1$ to $C_6$ ester.

22. The method of claim 21, wherein the fourth organic solvent is ethyl acetate.

23. The method of claim 20, wherein duloxetine oxalate is placed into a solution of the fourth organic solvent and water at a ratio of about 300 ml fourth organic solvent and water solution for about every 39 g of duloxetine oxalate.

24. The method of claim 20, wherein the solution of a fourth organic solvent and water contains about 1 ml fourth organic solvent for about every 1 ml water.

25. The method of claim 20, wherein the aqueous ammonia is added under stirring.

26. The method of claim 20, wherein an isolated aqueous layer is washed with the fourth organic solvent.

27. The method of claim 20, wherein the organic layer is dried with anhydrous sodium sulphate.

28. A method for the preparation of crystalline duloxetine hydrochloride, the method comprising:
(a) placing duloxetine oxalate into a solution of first organic solvent and water;
(b) adding aqueous ammonia solution for dissolving the duloxetine oxalate;
(c) isolating a separated organic layer;
(d) washing the organic layer with saturated brine;
(e) drying the organic layer;
(f) decolorizing the organic layer with a decolorizing agent;
(g) removing the decolorizing agent to form an organic solution;
(h) introducing gaseous hydrochloride into the organic solution; and
(i) collecting crystalline duloxetine hydrochloride from the organic solution.

29. The method of claim 28, wherein the first organic solvent is a $C_1$ to $C_6$ ester.

30. The method of claim 29, wherein the first organic solvent is ethyl acetate.

31. The method of claim 28, wherein duloxetine oxalate is placed into the solution of first organic solvent and water at a ratio of about 1 part solution of first organic solvent and water for about every 1 part duloxetine oxalate.

32. The method of claim 28, wherein the solution of first organic solvent and water contains about 1 ml first organic solvent for about every 1 ml water.

33. The method of claim 28, wherein the aqueous ammonia solution is added under stirring.

34. The method of claim 28, wherein the collected crystalline duloxetine hydrochloride is washed with a second organic solvent.

35. The method of claim 28, wherein the collected crystalline duloxetine hydrochloride is dried.

36. The method of claim 35, wherein the collected crystalline duloxetine hydrochloride is dried under vacuum.

37. The method of claim 28, wherein gaseous hydrochloride is introduced under agitation.

38. The method of claim 28, wherein gaseous hydrochloride is introduced until the organic solution reaches a pH of about 2 to about 4.

39. A method for the preparation of crystalline duloxetine hydrochloride, the method comprising:
(a) providing a solution of duloxetine free base in a first organic solvent to form an organic solution;
(b) mixing the organic solution with aqueous ammonium chloride solution; and
(c) acidifying the mixed solution to a pH of about 1 to about 4 with hydrochloric acid.

40. The method of claim 39, further comprising collecting crystalline duloxetine hydrochloride from the acidified organic solution.

41. The method of claim 40, further comprising, prior to collecting crystalline duloxetine hydrochloride from the acidified solution, isolating a separated organic layer.

42. The method of claim 41, further comprising, prior to collecting crystalline duloxetine hydrochloride from the organic solution, drying the isolated organic layer; decolorizing the organic layer with a decolorizing agent; removing the first organic solvent to form a residue; and dissolving the residue in a second organic solvent to form a second organic solution.

43. The method of claim 42, further comprising, prior to step (a):
  (a1) adding duloxetine oxalate to a mixture of a third organic solvent and water;
  (a2) adding aqueous ammonia solution for dissolving the duloxetine oxalate, and allowing an organic layer to separate from an aqueous layer;
  (a3) isolating the separated organic layer;
  (a4) saturating the aqueous layer with sodium chloride;
  (a5) extracting the aqueous layer with a fourth organic solvent to obtain an extracted organic layer;
  (a6) combining the separated and extracted organic layers to form a fifth organic solution; and
  (a7) washing the fifth organic solution with saturated brine.

44. The method of claim 39, wherein the duloxetine free base is provided in a first organic solvent selected from ethyl acetate, methyl acetate, dichloromethane, THF, methanol, ethanol, isopropanol, acetonitrile, hexane, heptane, chloroform, acetone, diethyl ether, diisopropyl ether, toluene, and mixtures thereof.

45. The method of claim 44, wherein the first organic solvent comprises ethyl acetate.

46. The method of claim 45, wherein the first organic solvent comprises a mixture of ethyl acetate and dichloromethane.

47. The method of claim 46, wherein the first organic solvent comprises 5:2 (w/w) ethyl acetate:dichloromethane.

48. The method of claim 39, wherein the ammonium chloride solution is a saturated solution.

49. The method of claim 39, wherein the hydrochloric acid is a dilute solution.

50. The method of claim 39, wherein the mixed solution is acidified to a pH of about 2 to about 4.

51. The method of claim 50, wherein the mixed solution is acidified to pH 2.

52. The method of claim 42, wherein the isolated organic layer is dried with anhydrous sodium sulphate.

53. The method of claim 42, wherein the decolorizing agent is active charcoal.

54. The method of claim 42, wherein the residue is formed by removing the first organic solvent by distillation under reduced pressure.

55. The method of claim 42, wherein the residue is a duloxetine hydrochloride residue and the second organic solvent is selected from ethyl acetate, methyl acetate, dichloromethane, THF, methanol, ethanol, isopropanol, acetonitrile, hexane, heptane, chloroform, acetone, diethyl ether, diisopropyl ether and toluene and mixtures thereof.

56. The method of claim 55, wherein the second organic solvent comprises ethyl acetate.

57. The method of claim 43, wherein:
  (i) the duloxetine oxalate is added to a mixture of ethyl acetate, dichloromethane and water;
  (ii) the aqueous layer is extracted with dichloromethane;
  (iii) the organic layer is dried with anhydrous sodium sulphate;
  (iv) the decolorizing agent is active charcoal;
  (v) the organic solvent is removed by distillation under reduced pressure to form a residue; and
  (vi) the residue is dissolved in ethyl acetate.

* * * * *